(12) United States Patent
Rombach

(10) Patent No.: US 7,850,308 B2
(45) Date of Patent: Dec. 14, 2010

(54) DEVICE AND METHOD FOR MEASURING THE OPTICAL PROPERTIES OF AN EYE IN COMBINATION WITH AN OPERATING MICROSCOPE

(75) Inventor: Michiel Christiaan Rombach, Breda (NL)

(73) Assignee: Akkolens International B.V. (NL)

( * ) Notice: Subject to any disclaimer, the term of this patent is extended or adjusted under 35 U.S.C. 154(b) by 166 days.

(21) Appl. No.: 11/851,357

(22) Filed: Sep. 6, 2007

(65) Prior Publication Data

US 2008/0062384 A1 Mar. 13, 2008

(30) Foreign Application Priority Data

Sep. 8, 2006 (NL) .................................. 2000221

(51) Int. Cl.
*A61B 3/10* (2006.01)
(52) U.S. Cl. ..................................................... 351/211
(58) Field of Classification Search ................. 351/203, 351/204, 205, 206, 210, 211, 212
See application file for complete search history.

(56) References Cited

U.S. PATENT DOCUMENTS

| | | |
|---|---|---|
| 2002/0135736 A1 | 9/2002 | Stark et al. |
| 2004/0239876 A1 | 12/2004 | Levine |
| 2005/0225750 A1 | 10/2005 | Dick et al. |
| 2005/0241653 A1 | 11/2005 | Van Heugten et al. |
| 2005/0243276 A1 | 11/2005 | Van Heugten |
| 2006/0017883 A1* | 1/2006 | Dai et al. ..................... 351/205 |
| 2006/0203196 A1 | 9/2006 | Van Heugten |

FOREIGN PATENT DOCUMENTS

| | | |
|---|---|---|
| AU | 763206 | 2/2000 |
| WO | 02/11612 A1 | 2/2002 |
| WO | 2005057252 A2 | 6/2005 |

\* cited by examiner

*Primary Examiner*—Timothy J Thompson
*Assistant Examiner*—Tuyen Q Tra
(74) *Attorney, Agent, or Firm*—DeMont & Breyer, LLC

(57) ABSTRACT

The invention relates to a device for measuring the optical properties of an eye, comprising an optical signal generator and optical guide means leading from the optical signal generator in the direction of the eye to be examined, wherein the optical signal generator is adapted to project an image through an optical path comprising the optical guide means and onto a reflective structure in the eye to be examined, wherein the device is adapted to couple the optical guide means of the device to optical guide means of an optical medical instrument so that the optical path extends through the optical guide means of the optical medical instrument. Such an optical medical instrument can be formed by an operating microscope, a so-called split lamp or by a fundus camera.

4 Claims, 3 Drawing Sheets

DEVICE AND METHOD FOR MEASURING THE OPTICAL PROPERTIES OF AN EYE IN COMBINATION WITH AN OPERATING MICROSCOPE

Measurements of the refraction of the eye in order to determine the dioptric strength of glasses and contact lenses to be fitted are standard procedures. Such measurements also take place before intra-ocular lenses are implanted. Intra-ocular lenses can be additional artificial lenses which function in combination with the natural lens of the eye (phakic intra-ocular lenses; usually implanted as replacement for glasses or contact lenses) or can be artificial lenses as replacement for the natural lens of the eye (aphakic intra-ocular lenses; usually implanted as replacement for the natural lens as a result of cataracts.

Relatively simple measurements of refraction of the eye give indications of the strength of the artificial lenses. The aim here is to correct the overall optics of the eye so that, in the case of a relaxed orbicular muscle which is coupled to the eye lens and the tissue related thereto (ciliary body), an overall optical strength is achieved such that the eye is focussed on infinity (emmetropia). In the know art measurements with a wavefront analysis are often applied, wherein various higher-order aberrations of the eye, which can possibly also be corrected with the additional optics, can also be analysed. Using these techniques the optical surfaces and structures, such as for instance the cornea of the eye, can also be visualized individually.

Cataracts are an opacity of the natural lens of the eye and occurs frequently. In the case of cataracts the natural lens is replaced with an artificial lens by an ophthalmic surgeon in relatively simple eye surgery. Such a measurement is also necessary prior to the surgical procedure in order to determine the optical strength of an intra-ocular artificial lens. The opacity of the lens often makes this measurement difficult, which can result in a deviation from the desired refraction of the eye after the operation. This deviation can generally be corrected with glasses, since after the operation cataract patients largely lose their ability to accommodate and will practically all wear glasses, certainly for situations in which high accommodation is desired, such as for instance reading. After the operation most cataract patients will generally have to wear so-called multifocal glasses with which a slight deviation of the artificial lens strength can also be corrected.

A measurement during the operation, followed by implantation of an artificial lens of a strength other than planned or, if the lens design allows, by adjustment of the optical strength of the artificial lens during the operation results in a better approximation of the desired strength of the artificial lens.

The natural eye lenses of long-sighted people (technical term: presbyopic patients; due to hardening of the natural lens this affects practically everyone over 40 years of age) are now also increasingly being replaced with artificial lenses which are either accommodating or have multifocal properties. The presbyopic patient then no longer needs reading glasses. However, the optical strength of these artificial lenses must here also be adjusted very precisely so as to prevent having to wear glasses later.

A number of accommodating artificial lenses for replacing the natural lens are now commercially available or are being clinically tested. These lenses can focus the eye via different optical principles, but are practically all driven by the ciliary orbicular muscle and related tissues of the eye, which are found to still function well even in patients at an advanced age. After implantation of an accommodating or multifocal lens the patient can in principle go through life without glasses. A practical drawback of these accommodating lenses is the fact that there are practically no possibilities for correction of optical strength of the artificial lens after the implantation of the artificial lens. The rest position of the artificial lens should in principle result in an emmetropic eye.

A number of adjustable artificial lenses are being developed. The optical strength of these lenses can still be adjusted during or after the implantation. This relates to both artificial lenses which are placed in the eye additionally to the natural lens, or to artificial lenses which replace the natural lens. WO-A-05084587 for instance describes intra-ocular artificial lenses which optionally replace the natural lens, and the optical strength of which can be adjusted during or after implantation.

The measurement of the optical strength and other optical characteristics of the eye before and after the operation takes place according to standard procedures and refraction measurements. The measurement of these optical properties of the eye during the operation has heretofore not been easy in practice. The patient lies under the operating microscope with an anaesthetized eye and there is no physical space for a refractive measurement, and for many ophthalmic surgeons a standard refraction measurement under these conditions results in an unacceptable disruption and delay of the surgical procedures.

In order to avoid these problems the present invention provides a device for measuring the optical properties of an eye, comprising an optical signal generator and optical guide means leading from the optical signal generator in the direction of the eye to be examined, wherein the optical signal generator is adapted to project an image through an optical path comprising the optical guide means and onto a reflective structure in the eye to be examined, wherein the device is adapted to couple the optical guide means of the device to optical guide means of an optical medical instrument so that the optical path extends through the optical guide means of the optical medical instrument.

These measures make it possible to perform the eye measurement by making use of common optical medical instruments supplied by a number of manufacturers. This has the result on the one hand that the necessary investment is lower through making use of the facilities of the already available instrument, and has the result on the other hand that less equipment is present in the vicinity of the eye during the measurement, so that possible operations in or on the eye are impeded less by the presence of equipment. An example of such an optical medical instrument is a so-called split lamp. The invention can otherwise also be applied in a fundus camera. It will be apparent that an optical path leading to the eye to be examined must be present in an optical medical instrument to be applied in the invention to enable application of the invention.

The invention also relates to a method for measuring the optical properties of an eye, wherein an image is projected through an optical path onto a reflective structure in the eye to be examined, the reflected image is cast through the optical path onto a sensor and the image cast onto the sensor is analysed, wherein the optical path extends through an optical medical instrument. The advantages of the invention are likewise obtained by applying this method.

The advantages of the invention become particularly manifest when the optical medical instrument is formed by an operating camera. This is because there is a need to measure the optical properties of the eye while performing an eye operation, for instance when placing an artificial lens.

According to another preferred embodiment, the device is adapted to project an image onto the retina of the eye to be examined. For most applications, including the above described applications, a measurement of the total refraction of the eye is desired, and the image reflected by the retina is analysed. Other reflections, for instance from the front and rear side of the cornea and surfaces of the eye lens, can in principle also be analysed using this method, particularly in an application which makes use of wavefront analysis. Thicknesses and shapes of different elements of the eye can also be measured with simple modifications. In all these variants the operating microscope forms an essential part of the device described here for measurements of the eye.

The measurements described in this patent application can also be applied not only in eye surgery, but also for instance for measurements of the eye for determining the strength and correction factors for glasses, a contact lens, or corrections which will take place in laser treatments of the cornea.

In the simplest embodiment it is possible for the ophthalmic surgeon to make an assessment of the optical qualities of the eye by observing the image projected onto the retina or another reflective structure in the eye by the optical signal generator, for which purpose use can be made of the ocular present in an operating microscope.

It is however recommended that the optical guide means are coupled by means of a beam splitter to an optical sensor, which is adapted to generate a signal representative of the image cast onto the sensor, and that the sensor is coupled to a computer which is adapted to analyse the image cast onto the sensor. An automated observation of the relevant image can take place with this optical sensor.

The beam splitter and the optical signal generator are preferably placed together in a housing and the housing is preferably placed on the side of the optical medical instrument directed toward the eye to be examined. In some optical medical instruments this setup can result in structural advantages, for instance by being coupled to the objective lens of the optical medical instrument. Due to such a construction the camera connection is also left clear for the primary function, i.e. taking photos or films of the eye operation.

It is however recommended that the beam splitter, the optical signal generator and the sensor are placed together in a housing, and that the housing is adapted to connect to a camera connection of the operating microscope. All parts of the device according to the invention can hereby be concentrated in a single apparatus, while use can be made of the camera connection already available on practically all operating microscopes.

By connecting the apparatus according to the invention to the camera connection of the operating microscope, the possibility to connect a cameras is lost. To avoid this disadvantage the apparatus comprises according to a specific embodiment an extra camera sensor. To throw an image onto the sensor surface use is made of an added beam splitter.

It will be apparent that the construction, which runs directly via the camera connection as described above, enables an optically simpler embodiment since provision is already made for in the design of the operating microscope for the optical alignment of the camera output. In a construction wherein the whole device, including the beam splitter, is coupled to the objective side of the microscope, the microscope still however remains an intrinsic part of the overall apparatus, since the surgeon can align and calibrate the beam of rays via the microscope and can visually observe the reflected image via the ocular.

Yet another preferred embodiment provides the measure that the sensor is formed by the sensor of a camera, wherein the camera is provided with a connection for generating a signal representative of the image cast onto the sensor. Depending on the equipment applied, this can be structurally attractive.

According to a specific embodiment, the combination of the sensor and the computer is adapted to measure the light intensity of an image cast onto the central part of the sensor. It hereby becomes possible to measure the total refraction of the eye, including the artificial lens. The computer is herein adapted to interpret the image and convert it into a measured value which analyses the correctness of the dioptric strength of the artificial lens.

For the purpose of measuring higher-order aberrations it can be attractive to make use of an embodiment in which the computer is adapted to determine optical properties of the measured eye from the result of the image analysis.

Yet another embodiment provides the measure that the sensor is adapted to analyse the optical properties of the eye on the basis of analysis of the wavefront of the light beam reflected by the eye to be examined and cast onto the sensor. The sensor can for instance be of the Shack-Hartmann type. Additional aberrations of different elements of the eye hereby not only become visible but can also be digitally analysed, and findings displayed quantitatively and in great detail.

The above stated wavefront analysis is preferably carried out with monochromatic or narrow-band light. For this purpose a preferred embodiment provides the measure that the signal generator is formed by a light source with a monochromatic character, such as for instance a laser light source.

As the reflections of the optical components of the eye are small, it is imperative that light is used of the considerable strength. In many cases this would lead to deterioration of the structure of the eye. To avoid this disadvantage it is preferred that the signal source is adapted to generate infra red light. Light of this wave length causes hardly damage to the eye.

The measuring process can be automated when a variably corrective element is placed in the optical path and the optical element is controlled such that the analysed image is as good as possible. This is then a type of fed-back control circuit. It is attractive for this purpose that an additional lens with a variable strength is placed in the optical path. This variable optical element can be operated by the user, the ophthalmic surgeon.

An optical element, of which the strength or more generally the optical properties can easily be varied, is a lens in accordance with the Alvarez principle. The additional lens is preferably formed by a lens in accordance with the Alvarez principle. This principle is described in the patent U.S. Pat. No. 4,305,294.

Although the device is in the first instance suitable for determining the optical strength, it is attractive to use the device for determining optical eye disorders of higher order, as long as the analysis of the image cast onto the sensor is adapted for this purpose. A preferred embodiment provides for this purpose the measure that the additional variable lens is adapted to compensate higher-order aberrations. This relates particularly, though not exclusively, to the correction of astigmatism, which is after all not only determined by the strength but also by an angle.

The above mentioned control circuit can be automated when the computer is adapted to vary the properties of the additional lens.

The present invention will now be elucidated with reference to the accompanying drawings, in which.

Figure 1:
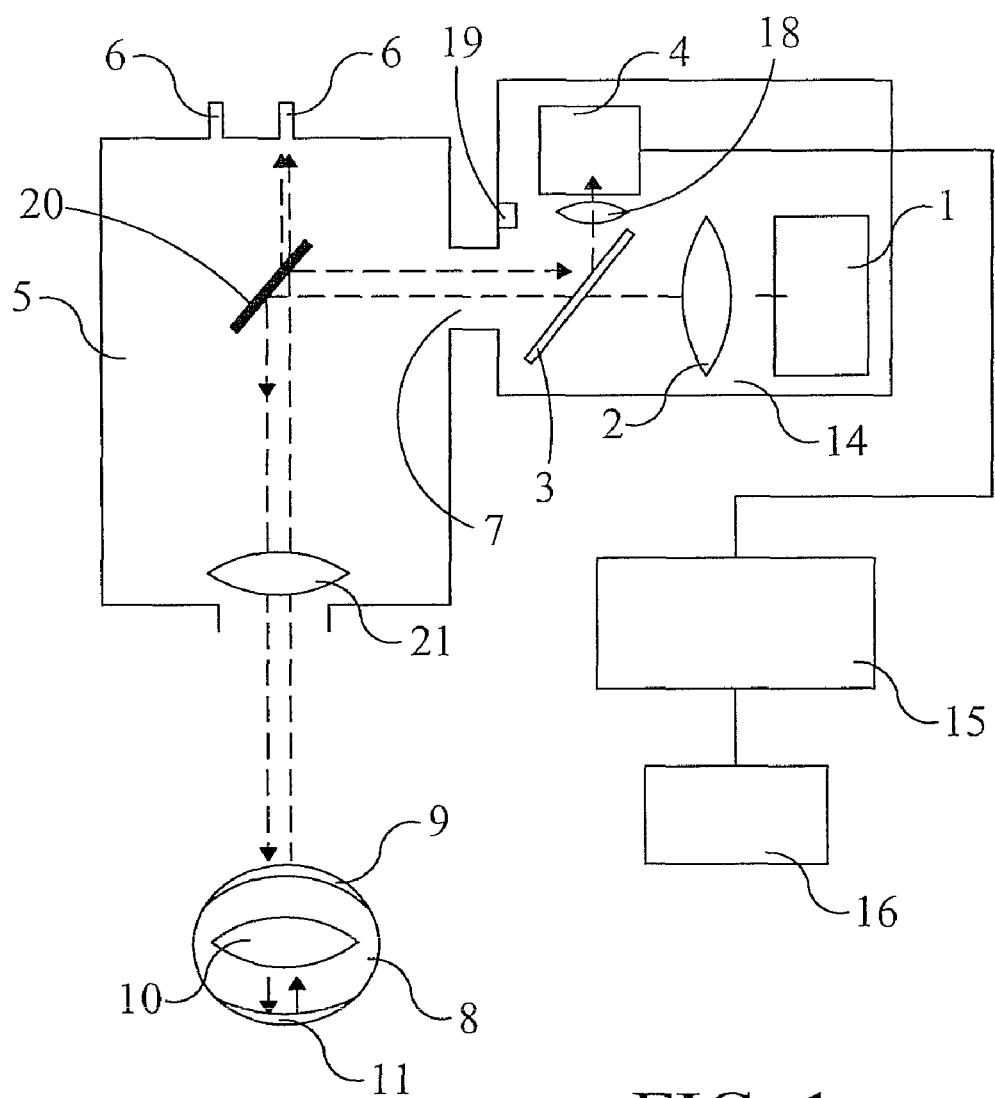
FIG. 1 shows a diagram of a device according to the invention.

The embodiment of the invention shown in FIG. 1 comprises an optical signal generator 1 in the form of a light source such as an LED, a laser source or other source of monochromatic or narrow-band light, preferably infra red light, a collimating lens 2, a beam splitter 3 and a sensor 4 in the form of a camera, a light-sensitive sensor or wavefront sensor.

The above described device, which is placed in a housing designated as a whole with 14, is adapted for placing on a per se known operating microscope 5 which is provided with an ocular 6 for the ophthalmic surgeon. The internal optics of the operating microscope are not shown in this schematic illustration. Operating microscope 5 comprises a so-called camera output 7, which is adapted for connection of a camera for making recordings of the eye while the eye operation is being performed, and a lens 21. A beam splitter 20 is further arranged in operating microscope 5. The device according to the invention is adapted for placing on camera connection 7 of operating microscope 5.

An image of the eye 8 including cornea 9, lens 10, which can be formed by the natural eye lens, by an artificial lens or by a combination of both, and retina 11 is thus formed on sensor 4 of device 14.

With the thus described combination of instruments an optical path is obtained which extends from the optical signal generator 4, via beam splitter 3, beam splitter 20 through optical parts of operating microscope 5 which are not shown in the drawing, into eye 8. An image generated by the optical signal generator is hereby cast onto retina 11 of eye 8. This optical path is indicated with arrows. The image projected onto the retina by the light source can take different forms. Use is made as an example in the embodiment in this patent of a wide collimated beam, although other forms can be envisaged and can provide optical and technical advantages.

This image is here subjected to the optical effects of cornea 9 and eye lens 10 of eye 8. This image is observed by the ophthalmic surgeon via ocular 6 of operating microscope 5. The image in question is also cast onto sensor 4. This image here also passes through the same optical path, wherein the eye lens once again influences the result. Sensor 4 is connected to a computer 15 and an imaging apparatus 16. The computer is used here to analyse the image cast onto sensor 4. The optical properties of the lens present in the eye during the measurement are determined on the basis of this analysis. These are in the first instance the strength of the eye lens, but also aberrations such as astigmatism. The effects of artificial lens can hereby be observed and measured during the operation for placing an artificial lens. If there is insufficient optical effect, another artificial lens can be selected. If the nature of the artificial lens is suitable therefor, it is also possible to adjust the artificial lens, for instance by rotating the artificial lens in order to correct for instance astigmatism. This option is also important in intra-ocular eye lenses, the strength of which can be adjusted, such as the lenses described in WO-A-05084587. The adjustment can here be optimized.

This first embodiment further comprises a variable optical element 18 which is arranged in the optical path, in the present case between beam splitter 12 and sensor 13. It is otherwise also possible to place the variable optical element 18 in different positions, otherwise also in the embodiment shown in FIG. 2. Depending on the result of the analysis of the optical qualities of the eye, the optical properties of optical element 18 can be adjusted here, for instance by placing another element or by changing the optical properties of the optical element by rotating or translating a part thereof. It is also possible in principle to make use of a drive device 19 to cause rotation or translation of the variable optical element 18. The drive device is preferably controlled by computer 16.

Figure 2:
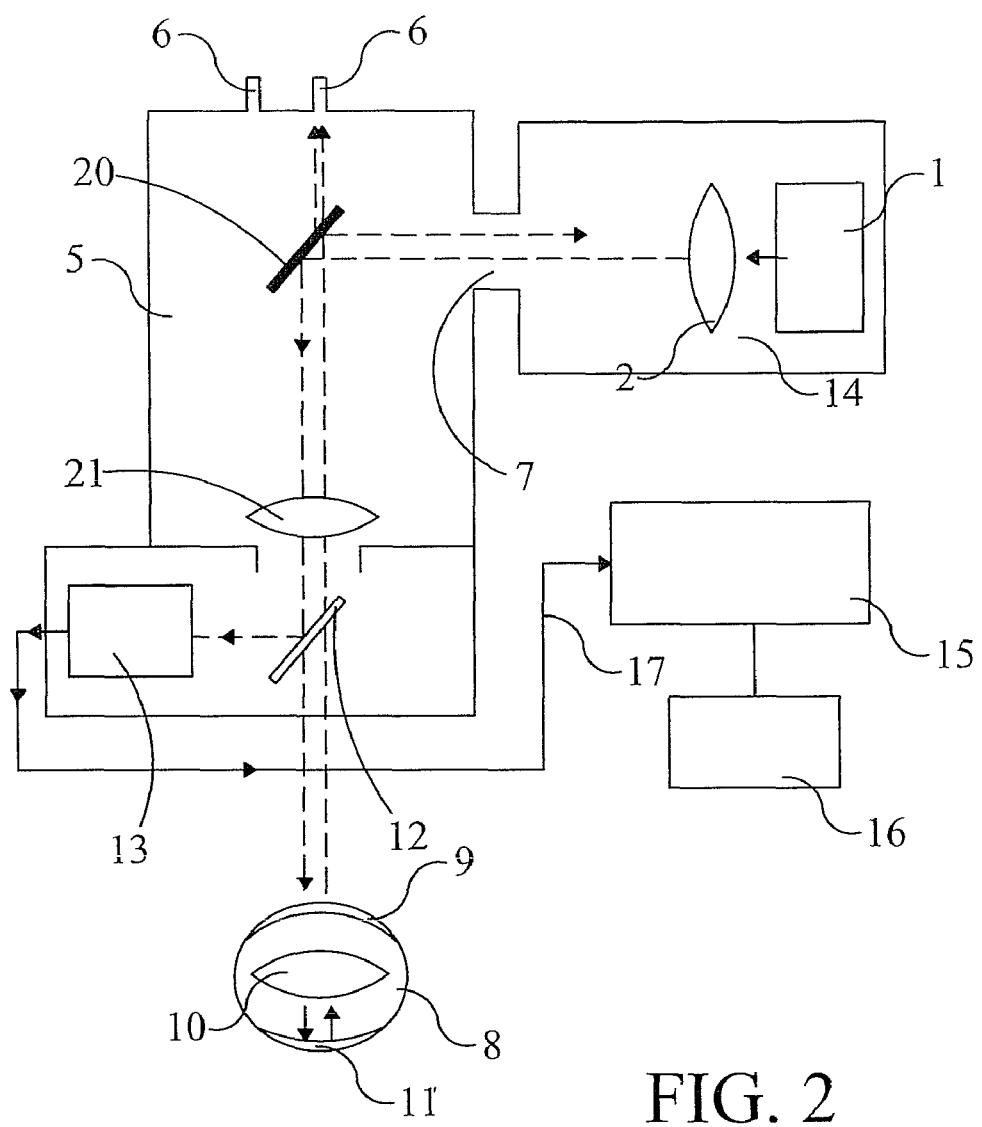
FIG. 2 shows a diagram of an alternative embodiment of the invention.

FIG. 2 shows an alternative device which differs from the device shown in FIG. 1 in the position of sensor 13, i.e. on the side of operating microscope 5 directed toward the eye. Beam splitter 12 is also arranged for this purpose at a different position. In this embodiment beam splitters 12 and the sensor are otherwise accommodated together in a housing 17 which is mounted against the side of the operating microscope directed toward the eye to be examined. This is a structural variation which may be attractive in determined types of operating microscope. A number of other variants are described above, but not all are each included in a separate illustration.

Figure 3:
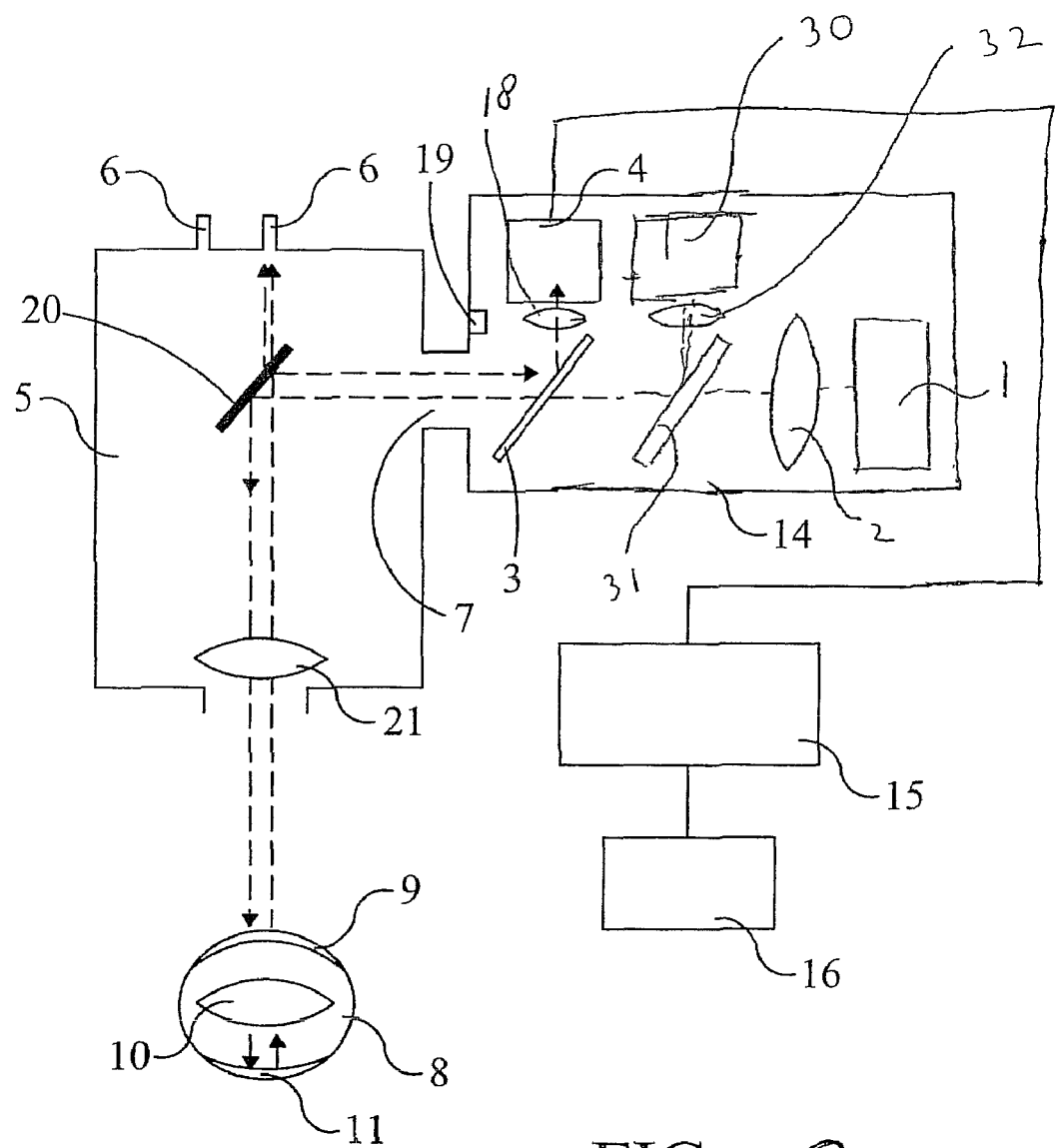
FIG. 3 shows a diagram of second alternative embodiment of the invention.

FIG. 3 depicts an alternative embodiment, deviating from the earlier embodiments by providing an extra camera 30 in the housing of the apparatus. The use of a camera connection of the operating microscope by the apparatus according to the invention precludes the possibility to connect a separate camera, for instance for recording the operation. Buy providing a camera in the apparatus according to the invention this disadvantage is avoided. To throw an image on the sensor 30 forming the camera, the is additional beam splitter 31 has been provided, which is adapted to let the conduct the light coming from the light source 1 and for reflecting to the sensor 30 the light coming from the beam splitter 3. Further use may be made of an additional lens 32.

The image cast onto the sensor can be disrupted by speckles of different intensity, whereby the analysis of the image is made more difficult. It is known to minimize or prevent this phenomenon by placing a filter with a diffuse effect (diffusor) between the laser and collimating lens. The phenomenon can likewise be decreased by placing a lens with a continuously oscillating focal distance. Such a lens can be formed by the lens with the variable focal distance as according to an embodiment of the invention. This lens will have to be provided for this purpose with a drive device which drives the lens in oscillating manner. The phenomenon can also be reduced by causing the light output of a laser incorporated in the light source to vary, for instance according to a sine function or a random function.

A lock-in amplifier or a narrow-band filter can further be applied in order to increase the signal/noise ratio. It is also possible to place a disc with openings, which rotates in synchronized manner, in front of the light source, for instance the laser, or to use a flash diode as light source. The signal/noise ratio can hereby be improved by up to a factor of 100.

The wavelength and intensity of the light source are important since they may of course under no circumstances cause damage to the eye of the patient or the eyes of the surgeon. This means a very low intensity of visible light or a selection of light of certain wavelength, for instance a laser with an output of <5 mW or infrared light which can be digitally analysed and converted into a visible image.

The invention claimed is:

1. Method for measuring the optical properties of an eye, comprising:
    projecting an image through an optical path onto a reflective structure in the eye to be examined;
    casting the reflected image through the optical path onto a sensor;
    converting the image that is cast onto the sensor into a signal;
    analysing the signal at a computer, resulting in a measurement result; and varying, through the computer and depending on the measurement result, optical properties of a variable lens placed in the optical path, followed by repeating the aforementioned steps to obtain a new measurement;
wherein the measuring takes place during a surgical operation of implanting an intra-ocular artificial lens, and wherein the optical path extends through an operating microscope.

2. Method as claimed in claim 1, characterized in that the optical properties of the eye, including the intra-ocular artificial lens placed in the eye, are measured.

3. Method as claimed in claim 2, characterized in that the optical properties of the intra-ocular artificial lens are adjusted subject to the measurement result.

4. Method as claimed in claim 2, characterized in that subject to the measurement result an intra-ocular artificial lens other than the intra-ocular artificial lens that is present in the eve during the measuring is selected for implantation.

* * * * *